(12) United States Patent
Haselman et al.

(10) Patent No.: US 8,309,932 B2
(45) Date of Patent: *Nov. 13, 2012

(54) DATA ACQUISITION FOR POSITRON EMISSION TOMOGRAPHY

(75) Inventors: Michael Haselman, Renton, WA (US); Robert S. Miyaoka, Shoreline, WA (US); Thomas K. Lewellen, Port Ludlow, WA (US); Scott Hauck, Seattle, WA (US)

(73) Assignee: University of Washington, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/213,007

(22) Filed: Aug. 18, 2011

(65) Prior Publication Data

US 2011/0301918 A1    Dec. 8, 2011

Related U.S. Application Data

(63) Continuation of application No. 12/264,093, filed on Nov. 3, 2008, now Pat. No. 8,003,948.

(60) Provisional application No. 60/985,083, filed on Nov. 2, 2007.

(51) Int. Cl.
*G01T 1/20* (2006.01)
*G01T 1/164* (2006.01)
*G01T 1/00* (2006.01)

(52) U.S. Cl. .................. 250/362; 250/363.03; 250/395

(58) Field of Classification Search .......... 250/362, 250/363.03, 395
See application file for complete search history.

(56) References Cited

U.S. PATENT DOCUMENTS

| 5,367,209 | A | 11/1994 | Hauck |
| 5,751,000 | A * | 5/1998 | McCroskey et al. ..... 250/363.03 |
| 6,014,509 | A | 1/2000 | Furtek |
| 7,129,497 | B2 | 10/2006 | Wollenweber |
| 7,411,199 | B2 | 8/2008 | Vernon |
| 7,630,528 | B2 | 12/2009 | Kohler |
| 2007/0057189 | A1 | 3/2007 | Jansen |

(Continued)

FOREIGN PATENT DOCUMENTS

JP    2005164334 A    6/2005

OTHER PUBLICATIONS

Abu-Aita, R.R., "Count Rate and Spatial Resolution Performance of a 3-Dimensional Dedicated Positron Emission Tomography Scanner," master's thesis, University of Florida, Gainesville, Fla., 2004, 120 pages.

(Continued)

*Primary Examiner* — David Porta
*Assistant Examiner* — Mindy Vu
(74) *Attorney, Agent, or Firm* — Christensen O'Connor Johnson Kindness PLLC

(57) ABSTRACT

A method for estimating the start time of an electronic pulse generated in response to a detected event, for example the start time for pulses received in response to photon detection in positron emission tomography, includes providing a detector that detects an external event and generates an electronic analog pulse signal. A composite reference pulse curve is calculated to represent analog pulse signals generated by the detector. Upon receiving an analog pulse signal, it may be filtered, and then digitized, and normalized based on the area of the digital signal. Using at least one point of the normalized digital pulse signal, the composite reference pulse curve shape is used to estimate the pulse start time.

28 Claims, 5 Drawing Sheets

U.S. PATENT DOCUMENTS

2008/0177191 A1    7/2008  Patangay

OTHER PUBLICATIONS

Haselman, M.D., et al., "FPGA-Based Data Acquisition System for a Positron Emission Tomography (PET) Scanner," Proceedings of the 16th ACM/SIGDA International Symposium on Field Programmable Gate Arrays, Monterey, Calif., Feb. 24-26, 2008, p. 264.

Haselman, M.D., et al., "FPGA-Based Front-End Electronics for Positron Emission Tomography," Proceedings of the ACM/SIGDA International Symposium on Field Programmable Gate Arrays, Monterey, Calif., Feb. 22-24, 2009, pp. 93-102.

Haselman, M.D., et al., "Simulation of Algorithms for Pulse Timing in FPGAs," Nuclear Science Symposium Conference Record 2007 (NSS '07), Honolulu, Hawaii, Oct. 26-Nov. 3, 2007, pp. 3161-3165.

Streun, M., et al., "Effects of Crosstalk and Gain Nonuniformity Using Multichannel PMTs in the Clearpet® Scanner," Nuclear Instruments and Methods in Physics Research A 537(1-2):402-405, Jan. 2005.

International Search Report and Written Opinion mailed Apr. 28, 2009, issued in corresponding International Application No. PCT/US2008/082273, filed Nov. 3, 2008, 7 pages.

\* cited by examiner

DATA ACQUISITION FOR POSITRON EMISSION TOMOGRAPHY

CROSS-REFERENCES TO RELATED APPLICATIONS

This application is a continuation of application Ser. No. 12/264,093, filed Nov. 3, 2008, which claims the benefit of Provisional Application No. 60/985,083, filed Nov. 2, 2007, the entire disclosures of which are hereby incorporated by reference herein.

STATEMENT OF GOVERNMENT LICENSE RIGHTS

This invention was made with Government support under #RO1 EB002117 awarded by the National Institutes of Health. The Government has certain rights in the invention.

BACKGROUND

The ability to produce images of the inside of a living organism without invasive surgery has been a major advancement in medicine over the last one hundred years. Imaging techniques such as X-ray computer tomography (CT) and magnetic resonance imaging (MRI) have given doctors and scientists the ability to view high-resolution images of anatomical structures inside the body. While this has led to advancements in disease diagnosis and treatment, a large set of diseases cause changes in anatomical structure only in the late stages of the disease, or never at all. This has given rise to a branch of medical imaging that captures certain metabolic activities inside a living body. Positron emission tomography (PET) is in this class of medical imaging.

Positron Emission Tomography

PET is a medical imaging modality that takes advantage of radioactive decays to measure certain metabolic activities inside living organisms. PET imaging systems comprise three main components, indicated schematically in FIG. 1, a radioactive tracer that is administered to the subject to be scanned, a scanner that is operable to detect the location of radioactive tracer (indirectly as discussed below), and a tomographic imaging processing system.

The first step is to produce and administer a radioactive tracer 90, comprising a radioactive isotope and a metabolically active molecule. The tracer 90 is injected into the body to be scanned 91. After allowing time for the tracer 90 to concentrate in certain tissues, the body 91 is suitably positioned inside the scanner 92. The radioactive decay event for tracers used in PET studies is positron emission. An emitted positron travels a short distance in the body tissue until it interacts with an electron. The positron-electron interaction in an annihilation event that produces two 511 KeV anti-parallel photons. The scanner 92 is adapted to detect at least some of the photons from the annihilation event.

The scanner 92, the second component of PET system, includes a ring of sensors that detect the 511 KeV photons, and front-end electronics that process the signals generated by the sensors. The sensors typically comprise scintillator crystals, or scintillators 93 and photomultiplier tubes (PMT), silicon photomultipliers (SiMP) or avalanche photo diodes (APD) 94. The scintillator crystal 93 converts the 511 KeV high-energy photons into many lower-energy photons, typically visible light photons. The PMT, SiMP or APD 94 detect the visible light photons and generate a corresponding electrical pulse. The PMT pulses are processed by front-end electronics to determine the parameters or characteristics of the pulse (i.e., energy, timing). For convenience, references to PMT herein will be understood to include any mechanism or device for detecting high-energy photons, such as 511 KeV photons, and producing lower-energy photons, such as visible light photons, in response.

Finally, the data is sent to a host computer 95 that performs tomographic image reconstruction to turn the data into a 3-D image.

Radiopharmaceutical

To synthesize the tracer 90, a short-lived radioactive isotope is attached to a metabolically active molecule. The short half-life reduces the subject's exposure to ionizing radiation, but generally requires the tracer 90 be produced close to the scanner. The most commonly used tracer is fluorine-18 flourodeoxyglucose ([F-18]FDG), an analog of glucose that has a half-life of 110 minutes. [F-18]FDG is similar enough to glucose that it is phosphorylated by cells that utilize glucose, but does not undergo glycolysis. Thus the radioactive portion of the molecule becomes trapped in the tissue. Cells that consume a lot of glucose, such as cancers and brain cells, accumulate more [F-18]FDG over time relative to other tissues.

After sufficient time has passed for the tissue of interest to uptake enough tracer 90, the scanner 92 is used to detect the radioactive decay events, i.e., by detecting the 511 KeV photons. When a positron is emitted, it typically travels a few millimeters in tissue before it annihilates with an electron, producing two 511 KeV photons directed at 180°±0.23° from one another.

Photon Scintillation

A 511 KeV photon has a substantial amount of energy and will pass through many materials, including body tissue. While this typically allows the photon to travel through and exit the body, the high-energy photons are difficult to detect. Photon detection is the task of the scintillator 93. A scintillator 93 absorbs high-energy photons and emits lower energy photons, typically visible light photons. A scintillator 93 can be made from various materials, including plastics, organic and inorganic crystals, and organic liquids. Each type of scintillator has a different density, index of refraction, timing characteristics, and wavelength of maximum emission.

In general, the density of the scintillator crystal determines how well the material stops the high-energy photons. The index of refraction of the scintillator crystal and the wavelength of the emitted light affect how easily light can be collected from the crystal. The wavelength of the emitted light also needs to be matched with the device that will turn the light into an electrical pulse (e.g., the PMT) in order to optimize the efficiency. The scintillator timing characteristics determine how long it takes the visible light to reach its maximum output (rise time) and how long it takes to decay (decay time). The rise and decay times are important because the longer the sum of these two times, the lower the number of events a detector can handle in a given period, and thus the longer the scan will take to get the same number of counts. Also, the longer the timing characteristics, the greater the likelihood that two events will overlap (pile-up) and data will be lost.

An exemplary modern scintillator material is $Lu_2SIo_5$ (Ce), or LSO, which is an inorganic crystal. LSO has a reported rise constant of 30 ps and a decay constant of 40 ns. The reported times can vary slightly due to variations in the geometry of the crystal and the electronics that are attached to it. LSO is a newer scintillator material that exhibits fast response and good light output.

Photomultiplier Tubes

Attached to the scintillator 93 are electronic devices that convert the visible light photons from the scintillator 93 into electronic pulses. The two most commonly used devices are PMTs and APDs. A PMT is a vacuum tube with a photocathode, several dynodes, and an anode that has high gains to allow very low levels of light to be detected. APDs are a semiconductor version of the PMT. Another technology that is currently being studied for use in PET scanners is SiPMs. SiPMs comprise an array of semiconducting photodiodes that operate in Geiger mode so that when a photon interacts and generates a carrier, a short pulse of current is generated. In an exemplary SiPM, the array of photodiodes comprises about 103 diodes per $mm^2$. All of the diodes are connected to a common silicon substrate so the output of the array is a sum of the output of all of the diodes. The output can therefore range from a minimum wherein one photodiode fires to a maximum wherein all of the photodiodes fire. This gives theses devices a linear output even though they are made up of digital devices.

An exemplary system uses a PMT having twelve channels: six in the 'x' direction and six in the 'y' direction, as depicted in FIG. 2. The separate channels allow for more accurately determining the location of an event. For example, if an event is detected in the upper left hand corner of the PMT, then channels Y1 and X1 will have a large signal, with progressively smaller signals at each successively larger channel number. Channels Y6 and X6 will have virtually no signal.

When enough coincidental events have been detected, image reconstruction can begin. Essentially the detected events are separated into parallel lines of response (interpreted path of photon pair), that can be used to create a 3-D image using computer tomography.

While PET, MRI, and CT are all common medical imaging techniques, the information obtained from the different modalities is quite different. MRI and CT give anatomical or structural information. That is, they produce a picture of the inside of the body. This is great for problems such as broken bones, torn ligaments or anything else that presents as abnormal structure. However, MRI and CT do not indicate metabolic activity. This is the domain of PET. The use of metabolically active tracers means that the images produced by PET provide functional or biochemical information.

Oncology (study of cancer) is currently the most common application of PET. Certain cancerous tissues metabolize more glucose than normal tissue. [F-18]FDG is close enough to glucose that cancerous cells readily absorb it, and therefore they have high radioactive activity relative to background tissue during a scan. This enables a PET scan to detect some cancers before they are large enough to be seen on an MRI scan. PET scan information is also very useful for monitoring treatment progression, as the quantity of tracer uptake can be tracked over the progression of the therapy. If a scan indicates lower activity in the same cancerous tissue after therapy, it indicates the therapy is working.

PET is also useful in neurology (study of the nervous system) and cardiology (study of the heart). An interesting application in neurology is the early diagnosis of Parkinson's disease. Tracers have been developed that concentrate in the cells in the brain that produce dopamine, a neurotransmitter. In patients with Parkinson's disease, neurons that produce dopamine reduce in number. So, a scan of a Parkinson's patient would have less activity than a healthy patient. This can lead to early diagnosis, since many of the other early signs of Parkinson's are similar to other diseases.

There remains a need for continued improvements in the cost, efficiency and accuracy of PET systems.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method is disclosed for estimating the start time of electronic pulses, such as pulses generated from detecting high-energy photons in positron emission tomography, wherein very accurate start time information is beneficial. Detectors are provided for detecting an external event such as the incidence of photons on the detector, and generating an electronic analog pulse signal. A composite reference pulse curve shape is generated to represent the analog pulse signals generated by the detectors. On receiving an analog pulse signal, it is digitized with an ADC, to produce a digital pulse signal. The amplitude of the digital pulse signal values are then normalized based on the area of the calculated area of the digital pulse signal. For example, the discrete values that comprise the digital pulse signal may be scaled by the ratio of the calculated area to the normalized curve area. Using at least one point from the normalized pulse signal, the composite reference pulse curve shape is used to estimate the start time of the received analog pulse signal. It will be appreciated that in general the start time will be intermediate of points in the digital pulse signal. A time stamp for the analog pulse signal may then be recorded.

In an embodiment of the invention the analog pulse signal is generated by a silicon photomultiplier.

In an embodiment of the invention the only the first point of the digital pulse signal is used to specify the curve.

In an embodiment of the invention the analog pulse signal is filtered with a low-pass filter prior to digitizing the signal.

In an embodiment of the invention a reverse lookup is used, wherein one or more lookup tables hold the start time estimate for a set of normalized signal point amplitudes.

In an embodiment of the invention the detectors comprise a scintillator crystal coupled to one of a photomultiplier tube, an avalanche photodiode and a silicon photomultiplier.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
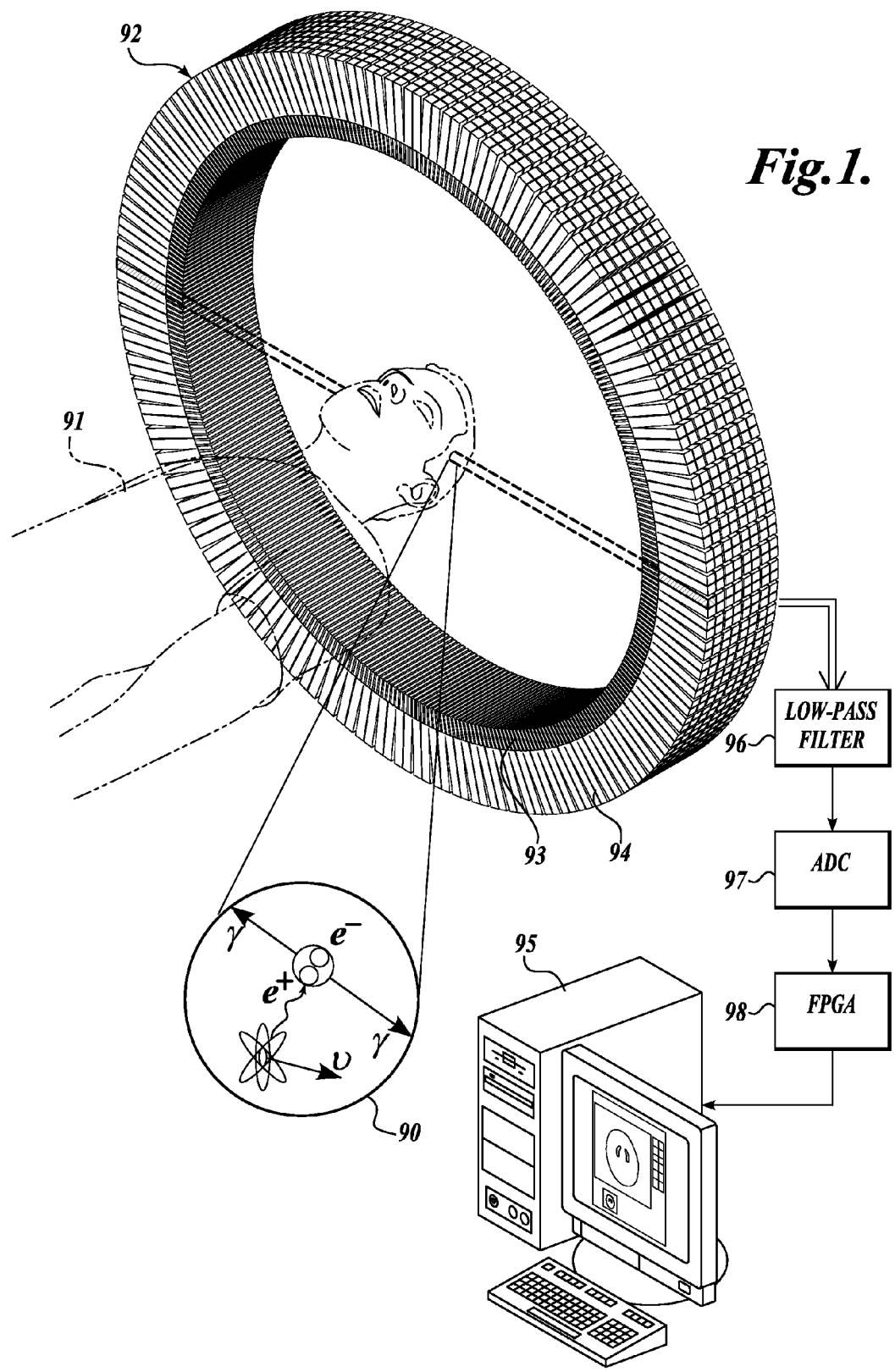
FIG. 1 is an environmental view showing a PET scanner system in accordance with the present invention.

A description of particular embodiments of a PET system in accordance with the present invention will now be described with reference to the FIGURES, wherein like numbers indicate like parts. Referring again to FIG. 1, a high-resolution PET scanner 92 is disclosed with detectors comprising scintillators 93 and PMTs 94. Sensor data is filtered with a low-pass filter 96, digitized with an analog to digital converter 97, and the digitized data is initially processed with field programmable gate arrays (FPGAs) 98.

The analog pulses generated by the PMTs 94 contain the information used to create a PET image. The analog pulses are processed to extract start time, location, and total energy. The apparatus for performing this initial processing is referred to the front-end electronics, and includes the filters 96, ADCs 97, and FPGAs 98. The analog pulse received from the PMT 94 is filtered with the low pass filter 96 to remove noise, and then digitized with the ADC 97, for processing by the FPGA 98. Even though some modern ADCs can sample at rates of up to 400 mega samples per second (MSPS), in a current embodiment a serial ADC 97 that samples at 70 MSPS is selected. This selection significantly reduces the complexity, cost and power consumption of the PET design. Another consideration is the number of inputs to the FPGA 98. Very fast ADCs have a parallel output which would require 10-12 bits per channel, with tens to hundreds of channels per FPGA. The number of inputs would thus outnumber the amount that even modern FPGAs can handle. Therefore, the current system uses serial output ADCs 97, which limits the sampling rate to around 100 MSPS. However, for systems requiring fewer ADCs per FPGA, faster ADCs can be used to achieve better timing resolution.

After the analog pulse data is digitized, the requisite pulse parameters can be extracted in the FPGA 98. A total pulse energy, for example, may be obtained by summing the samples of the pulse values and subtracting out the baseline (the output value of the ADC 97 without an input pulse).

The start time of the pulse is important for determining coincidence pairs, i.e., two detected photons that arise from a single annihilation event. It will be appreciated by persons of skill in the art that many photons generated by annihilation events are not detected by the scanner 92. For example, the generated photon may be either absorbed or scattered by body tissue or may travel along a path that does not intersect a scintillator 93. PET image generation requires detecting both photons of an annihilation event, because the path of the detected photons is then known to be substantially on a line between the detected photons. If only one of the two emitted photons is detected by the scanner 92, there is no way to determine where the event occurred. If two detected photons are a coincident pair, they must be detected within a certain time of each other and each of the detectors must be located within the field of view of the other.

An exemplary, high-resolution, small animal PET scanner has been constructed, comprising a ring of eighteen detector cassettes, with each cassette having four scintillator 93 arrays attached to four PMTs 94. Each detector cassette is connected to a dedicated set of front-end electronics.

Figure 3:
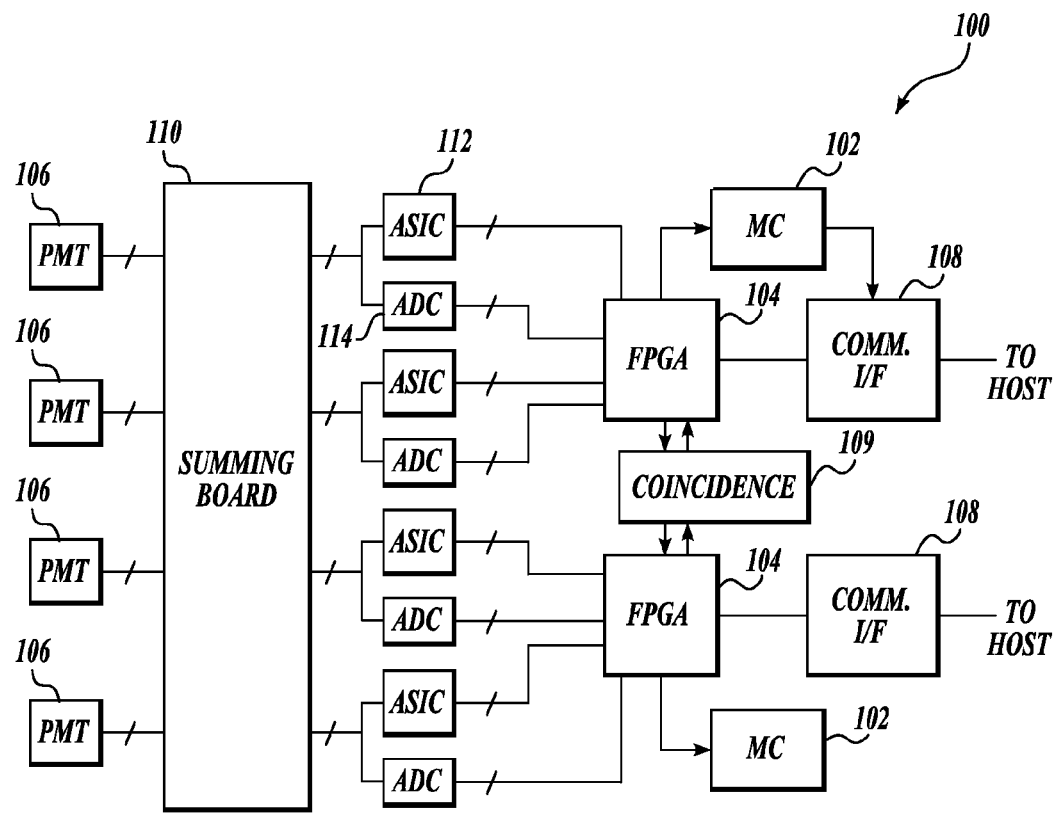
FIG. 3 is a block diagram showing the architecture of the front-end electronics for one embodiment of a high-resolution PET scanner in accordance with the present invention.

A schematic block diagram of the front-end electronics 100 for the exemplary small animal scanner is shown in FIG. 3. The front end electronics 100 comprise a number of "nodes" (two shown) comprising a microprocessor 102 and FPGA 104 pair. Each node supports two PMTs 106. All the nodes are daisy chained together using a standard high-speed communications interface 108, for example using the IEEE 1394a interface, such as the FireWire® implementation, to create a connection to the host computer (not shown). The host computer contains software that collects and processes data from all of the nodes. The data is subsequently processed off-line to produce the desired image.

Figure 2:
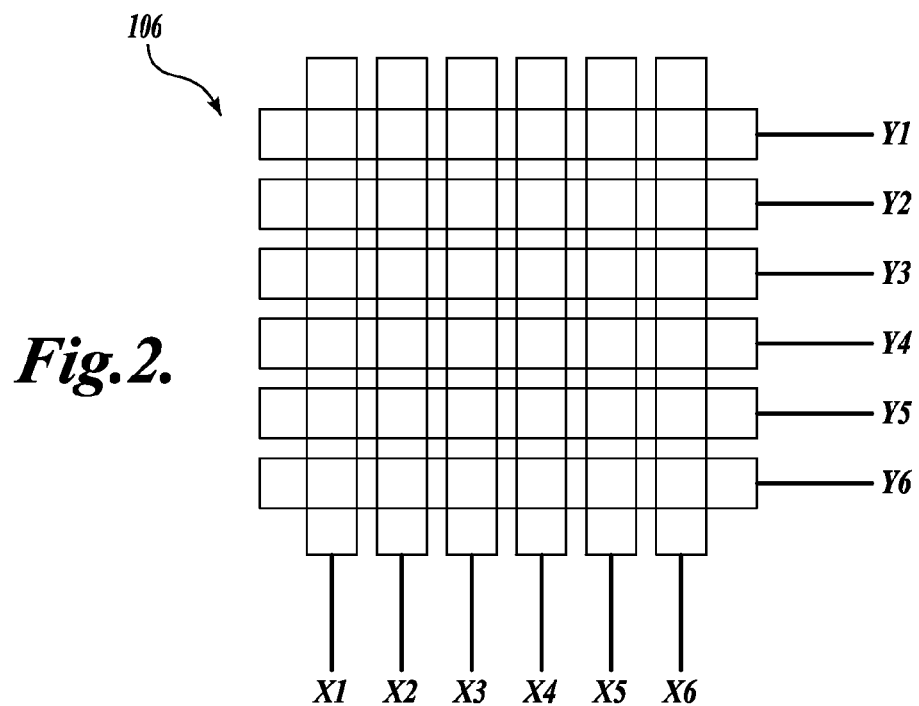
FIG. 2 illustrates the output channels of an exemplary twelve-channel PMT, with six channels in an 'x' direction and six channels in an orthogonal 'y' direction.

As shown in FIG. 3, there are many discrete parts to the front-end electronics 100. The PMTs 106 detect the light from the scintillator crystals (not shown in FIG. 3) and produce corresponding analog pulses. Each PMT 106 outputs twelve signals, six for the x direction and six for the y directions (see, FIG. 2). In a current embodiment, to reduce I/O counts, the twelve signals are reduced to four with a summing board 110. ASICs 112 receive the data and implement an algorithm to determine the time of a detected event. The signals are digitized by ADCs 114, and sent to the FPGAs 104. A coincidence unit 109 is optionally provided to identify pairs of events that may be coincident, filtering out events that clearly are not useful for further processing.

In addition to the FPGAs 104, there is a microprocessor 102 (currently using a Rabbit™ microcontroller) and a communications interface physical layer chip 108 used for communication to the host computer. The FPGA 104 and microprocessor 102 play a central role in the data acquisition. The microprocessor 102 provides general control of each individual node. This includes configuring the FPGAs 104, communicating with the host computer, initializing the system, and working with the FPGA 104 to tune the system. While the microprocessors 102 handle the control of the system, the FPGAs 104 make up the bulk of the data path. During normal operation, the FPGAs 104 have two primary tasks: pulse processing and data packing for the communications interface 108. For pulse processing the first step is to determine if a given event is in coincidence with another event on the other side of the scanner 92. If a matching coincidence event is detected, the pulse is integrated to determine the energy, and a coarse resolution time stamp is put on the data. The energy and time (coarse grain from the FPGA and fine grain from the ASIC) are sent to the host computer over the communications interface 108.

Occasionally, the scanner 92 needs to be tuned to set the amplifier gains in the ASICs 112. This is required because the scintillator crystals 93 have different light output and light collection efficiencies and the PMTs 106 have different gain characteristics. The tuning normalizes the differences between the sensors and corrects for drift over time. To tune the scanner, the microprocessor 102 reconfigures the FPGAs 104 using a tuning algorithm, and initializes the FPGAs 104 to bin up the energy values for each pulse. Unfortunately, edge effects near the periphery of the scintillator crystal array 93 and PMT 106 can introduce errors into the tuning algorithm, and are therefore ignored. In order to filter out the events that hit the edge of the crystal array, the position of the event must be decoded. The four signals that come from the summing board 110 contain enough information to determine the position of the event in the crystal array 93.

Once an event is determined to be in the interesting area of the scintillator crystal array 93, the total energy of the event is calculated and it is placed into different energy bins. This produces an energy histogram having a peak, referred to as the photo peak (because it represents the energy when all of the energy from the 511 KeV photon is deposited into the scintillator crystal). Counts below the photopeak represent scattered photons, where either only part of the energy of the photon is deposited in the crystal or the photon Compton scatters in the object being imaged before it reaches the crystal.

If the system is tuned, the photo peaks should line up for all of the detectors. If the peaks have some variations, the microprocessor changes the gains and reruns the tuning algorithm. This is all automated, so once the operator instructs the machine to tune itself, the microprocessor 102 will instruct the FPGAs 104 to run the tuning algorithm. Once the FPGA 104 signals that the routine has completed, the microprocessor 102 reads the histogram out of memory and locates the photo peak. If the photo peak is shifted, the microprocessor 102 adjusts the gains in the ASIC 112 and iterates until the photo peaks for all of the sensors line up.

Figure 4:
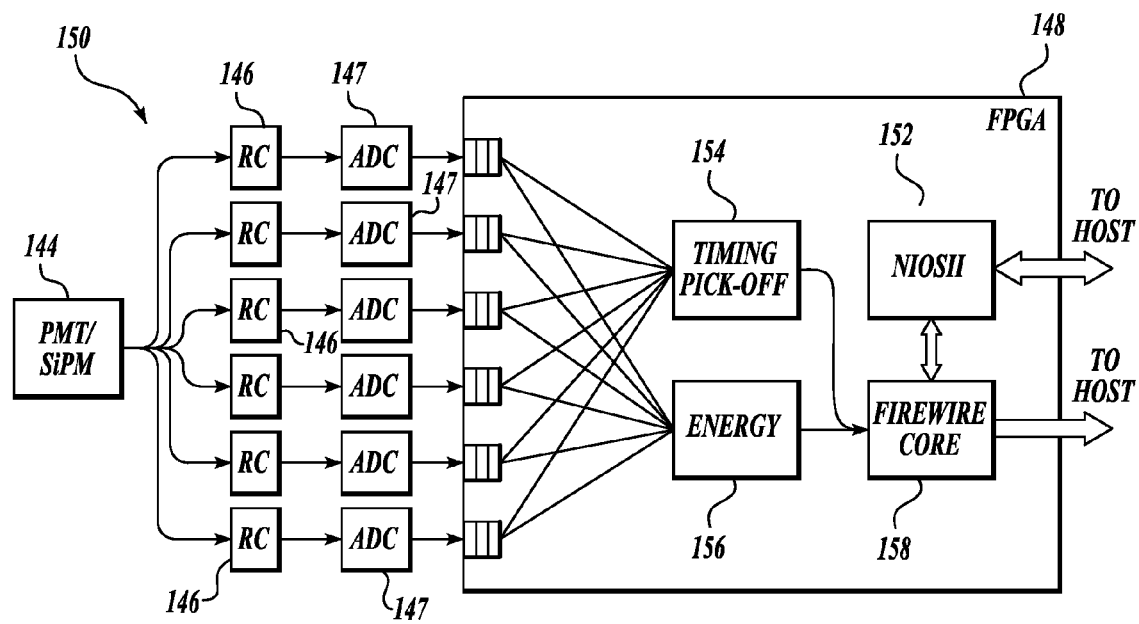
FIG. 4 is a block diagram showing the architecture of the front-end electronics for a second embodiment of a high-resolution PET scanner in accordance with the present invention.

In a second embodiment of a PET scanning system illustrated in FIG. 4, the photomultiplier devices 144 are solid state SiPMs having one output per crystal, which greatly increases the number of channels that will be used per sensor. FIG. 4 is a schematic block diagram showing the front end electronics 150 for this second embodiment. For this second embodiment, a Stratix® II EPS60 FPGA 148, and 70 MHz serial ADC 147 were selected, which can easily communicate using the dedicated serializer/deserializer and phase lock loops. In this embodiment, most of the front-end electronic functionality is performed by the FPGA 148, providing a much simpler, more compact architecture. The filters 146 are shown as simple RC filters, although clearly other filters may be used, as are well-known in the art.

There are other aspects of these more modern FPGAs 148 that make them perfectly suited to the PET system front-end application. For example, the Rabbit™ microprocessor 102 is replaced with a Nios® II 152 soft core embedded processor in the FPGA 148, eliminating the slow communication speed between the FPGA 104 and the microprocessor 102 of the architecture shown in FIG. 3. As will be apparent by comparing FIG. 4 with FIG. 2, the front end electronics 150 architecture of this second embodiment scanner is more compact due to the integration of parts into the FPGA 148, which includes the timing pickoff logic 154, the energy calculation logic 156 and the FireWire® core 158, in addition to the embedded processor 152.

Another consequence of having a large number of channels is that the cost and board space required to have a timing ASIC for each of the channels would be prohibitive. This has led to the development of an algorithm to perform the complete timing inside the FPGA 148.

An important objective for producing high-quality PET images is to precisely determine the timing of the photons interacting with the scintillator crystal 93. The timing resolution is directly correlated to the number of non-coincidental events that are accepted as good events, and thus add to the noise of the final image. In this second embodiment, the timing is accomplished in the FPGA 148 with sampled data, eliminating the need for the per-channel ASICs.

Figure 5:
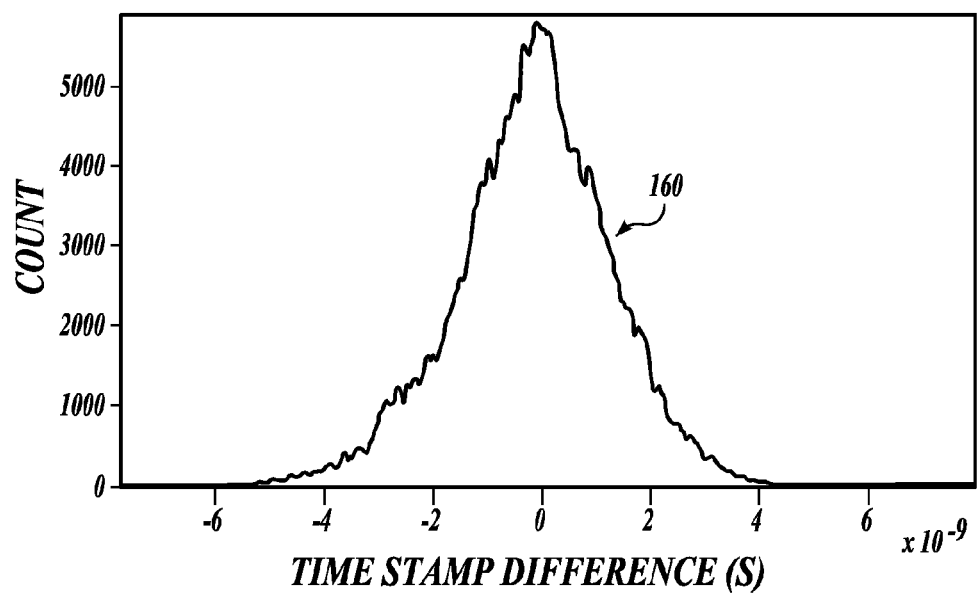
FIG. 5 shows the distribution of difference of time stamps for pulses for a sampling rate of 70 MHz using the method of the present invention.

The figure of merit for timing pick-off is the distribution of the times stamps. In other words, for a setup with two detectors with a source exactly centered between them (so photons arrive both detectors at the same time), we analyze the distribution of the differences between the time stamps for each detector. For an ideal system, the difference between the time stamps would be zero. However, noise in the system will introduce errors. To simulate this, time stamps were calculated for many different samplings of the same pulse. The time stamps for each pulse where then compared to the time stamps of all other pulses to produce a distribution 160 of time stamp differences, as shown in FIG. 5.

To determine the timing of a photon interacting with the scintillators 93, a timing pick-off circuit 156 is used. A timing pickoff circuit 156 assigns a time stamp to a particular feature of a detected pulse signal received from the PMT. For example, this feature could be the pulse start time, the pulse peak value time, or the time the pulse crosses a predetermined voltage. The two traditional techniques for timing pick-off are leading edge and constant fraction discriminators (CFD). Leading edge is simply determining when the pulse has crossed a certain fixed threshold voltage. This requires an analog circuit that detects the crossing. The drawback of this technique is that the time to reach the threshold is dependent on the amplitude of the pulse. This effect gets worse as the trigger level is set higher.

Current state of the art timing pick-off for PET systems is performed with analog CFDs because they are immune to pulse amplitude variance. A CFD implements a circuit for the following equation:

$$h(t) = \delta(t-D) - CF \cdot \delta(t)$$

where, $\delta(t)$ is the incoming signal. The equation is computed by splitting the analog pulse into two copies, and delaying one copy by D. The other copy is inverted and attenuated by a constant fraction (typically ~0.2). Finally, the two altered copies are added to produce a pulse with a zero crossing that can be detected and time stamped. The zero crossing occurs at a constant fraction of the pulse amplitude for pulses with the same shape. Both CFD and leading edge are typically done in dedicated ASICs, and require a circuit to convert the trigger to a time stamp. CFDs can achieve sub-nanosecond timing resolution.

Timing Pick-Off Method

A method is disclosed herein for using the known characteristics of the pulses to compute the start of the pulse, thereby achieving sub-sampling timing resolution. For LSO scintillator crystals, for example, the rise time is dominated by the response of the PMT, while the decay time is a function of the scintillation crystal. Based on these assumptions, the start time of the pulse can be determined by fitting an ideal pulse to the sampled pulse and using the ideal pulse to interpolate the starting point of the pulse.

To test this timing algorithms on real data, a 25 Gs/s oscilloscope was used to sample nineteen pulses from a PMT that was coupled to an LSO crystal. A 511 KeV (22 Na) source was used to generate the pulses. The data from the oscilloscope was then imported into MATLAB®.

A model curve that provides a good fit to the pulse data is a two exponential curve, e.g.:

$$V(n) = A\left(\exp^{\frac{-n*T_S}{\tau_R}} - \exp^{\frac{-n*T_S}{\tau_F}}\right)$$

As an initial step, we hypothesized that if we created a pulse with two exponentials (one for the rising edge and one for the falling edge) and found the amplitude, time shift, decaying exponential and rising exponentials that produced the best least squares fit to the measured digital pulse data, we could define an ideal pulse and use it to interpolate the starting point of the pulse. Using this "brute force" method, the standard deviation of the timing pick-off was 1.0 ns with a 70 MHz ADC. While this is good timing resolution, the search space is far too large for an FPGA to compute in real time. From the "brute force" method, we found that the rise time ranged from 0.1-0.5 ns, the decay times ranged from 28-38 ns, and the amplitude ranged from 0.082-0.185V. To cover these ranges for a reasonable time step (~40 ps) would require the least squares fit to be calculated and compared at least 215,000 times for each pulse (11 decay time steps, 5 rise time steps, 11 amplitude steps and 357 time steps).

To develop a more efficient FPGA-based algorithm and method, first assume that the rise and decay times, $\tau_R, \tau_F$ of the PMT/SiPM pulses are constants and the variability in the pulses is from the pulse amplitude and white noise.

For example, in our test apparatus, the rise and decay times that gave the best overall least squares fit for all unfiltered, unsampled data (i.e., raw data from the oscilloscope) were 310 ps and 34.5 ns, respectively. Using fixed rise and decay times, with the "brute force" method, the standard deviation of the timing pick-off degrades to 1.1 ns. However, even after eliminating the time constant searches, almost 4,000 searches would still be required for each event.

Figure 6:
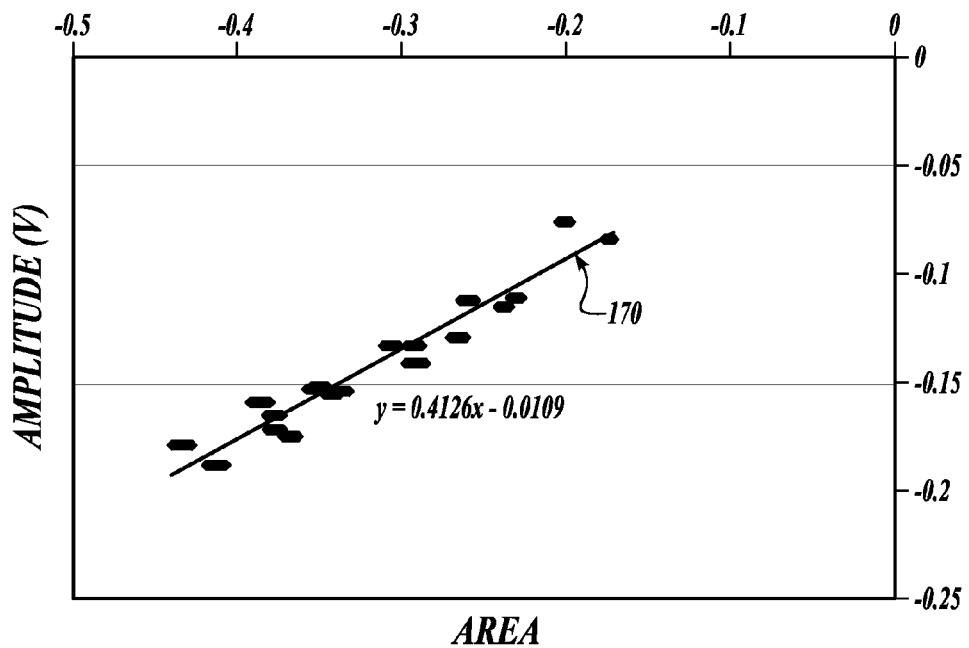
FIG. 6 shows a correlation between the filtered pulses and the amplitude of the pulses, and indicating a bet linear fit estimate of the correlation.

To further simplify the method, we eliminate the difference in amplitude for the reference pulse (defined by the two exponential equation) and the incoming data pulse using a direct correlation between the area and amplitude of the pulse. There is a good direct correlation 170 between the area of the detected pulse and amplitude of the pulse, as shown in FIG. 6. To normalize the amplitude of an event to the reference pulse, the ratio of the reference pulse area to the event pulse area is calculated. The event pulse can them be scaled by the ratio to equalize the amplitude of the reference and event pulses. For example, the area of a digitized event pulse may be calculated, and compared to the area of the ideal reference pulse. The event pulse sample points may then be scaled or normalized according to the ratio of the two areas. The normalized digital event pulse may then be used to estimate the start time of the event pulse by comparing the normalized event pulse values with the reference pulse.

A function to convert area to amplitude was determined by sampling each of the nineteen pulses with many different starting points, and correlating the area obtained for each sampling to the known amplitude for that complete pulse. Using this estimation, the standard deviation of the timing pick-off is degraded to 1.2 ns.

Using these two approximations, most dimensions of the brute-force search have been eliminated with a loss of only 20% timing resolution. However, this algorithm would still require 357 searches for each possible timing offset. Given that the pulse data is fit to a reference curve with known rise and decay times, and the amplitude is computed from the pulse area, the brute force search may be converted to a reverse-lookup.

Consider, for example, a pulse having a length of about $2 \times 10^{-7}$ seconds, sampled at 70 MHz, resulting in about thirteen sample points. For each possible input voltage the time it occurs on the reference pulse is pre-calculated. Thus, each incoming voltage can be converted to a timing offset with a simple memory operation. This is done for each pulse so that after the lookup, any or all of the thirteen sample points can be used to estimate the time at which the pulse started. If these thirteen start times are averaged, the timing resolution degrades significantly to 2.84 ns.

Figure 7:
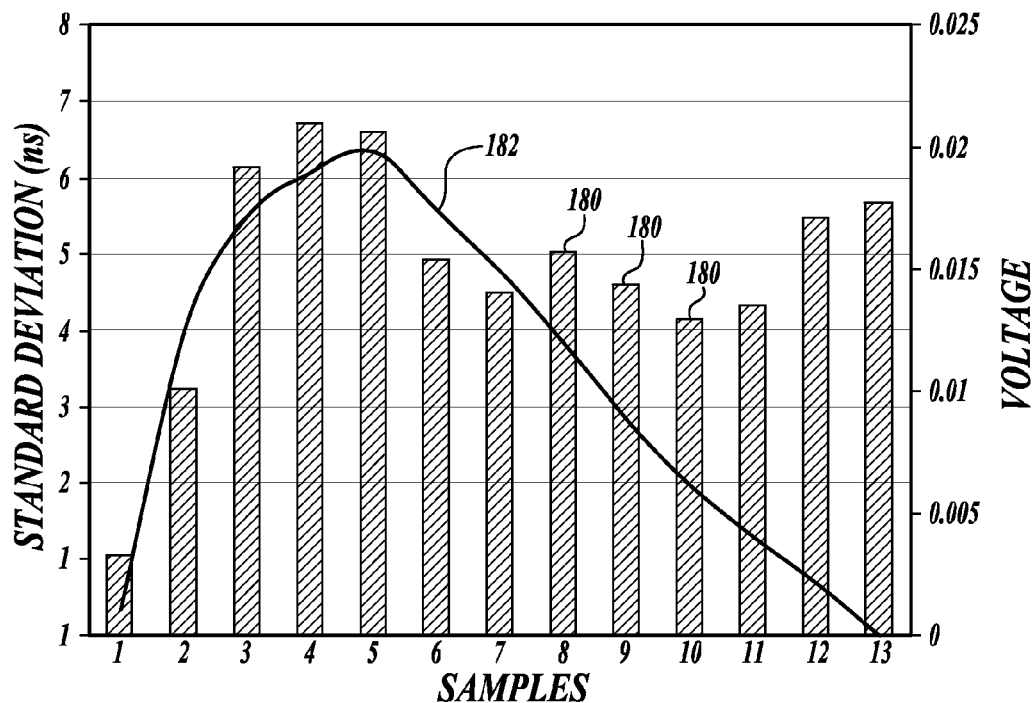
FIG. 7 is a plot of the standard deviation of the points of a filtered pulse that is sampled with a 70 MHz ADC, with a line indicating a filtered pulse (inverted) to give a reference for each point's position on the pulse.

After a close inspection of the results from our look-up method, it became apparent that some of the sample points give much better results than others. This is shown in FIG. 7, which plots the standard deviation 180 of the calculated start times for each of the thirteen sample points. From FIG. 7, the standard deviation 180 is correlated with the slope of filtered pulse 182, and distance from the pulse start. Points near the peak (samples 4 and 5) have a low slope, and thus a small change in voltage results in a large time shift. The tail of the pulse also has a large deviation. If only the first sample point is used, however, the standard deviation of the timing pick-off is 1.03 ns, which essentially equals the "brute force" method.

Using this information, the reverse look-up step was changed to only use the first sample point above 0.005V on the detected pulse. However, with faster ADCs or pulses with slower rise times more sample points can be averaged or otherwise correlated to produce a better final result.

Therefore, the current timing algorithm uses one decay constant, one rising constant, calculates the pulse amplitude from the area, and uses the voltage-to-time look-up for the first sample. In tests, this algorithm produces a standard deviation of the timing pick-off of only 1.03 ns. The distribution of the final algorithm is shown in FIG. 5 for a 70 MHz ADC. Although the use of only the first sample point produces very good results, it will be readily apparent to persons of skill in the art that in some circumstances the pick-off estimate may be improved using a weighted average of more than one of the sample points. For example, in another embodiment of the present invention the first two or three sample points may be used with experimentally derived weighting to further improve the consistency of the timing pick off.

Figure 8:
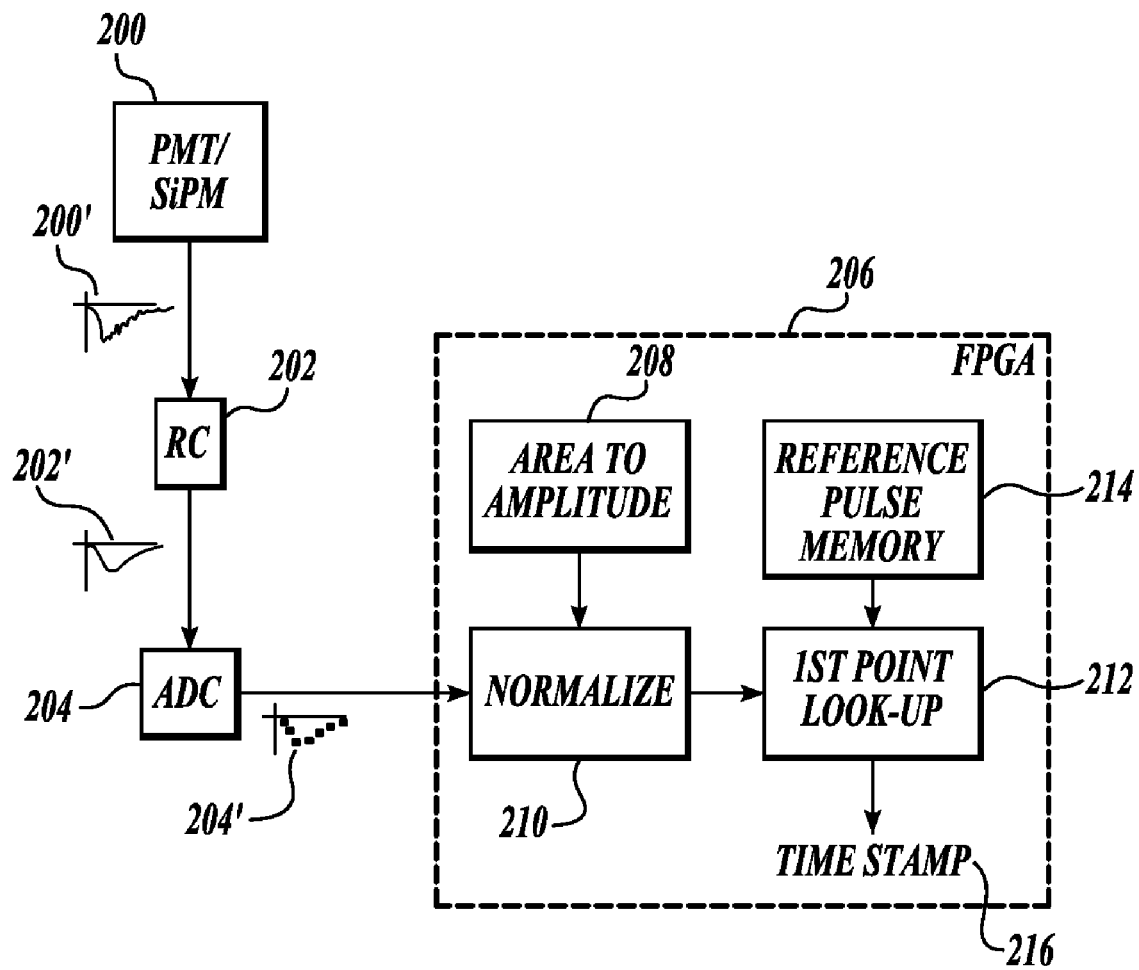
FIG. 8 is a block diagram showing an architecture of the timing pick-off circuit implemented in the FPGA for the system shown in FIG. 4.

The implementation architecture of timing algorithm is shown in FIG. 8. The PMT 200 such as an SiPM receives the pulse signal from the scintillator and generates an output pulse (represented by noisy signal 200'), which is filtered, typically with a low pass filter 202 (represented by smoother signal 202'), and then digitized with an ADC 204 (represented by digital signal 204'). The digital signal 204' is sent to the FPGA 206. The FPGA 206 is coded to calculate the area of the detected signal, and the area/amplitude correlation is used to estimate the signal amplitude 208. The signal can then be normalized 210 to the reference pulse's area. A selected data point (or set of points) from the digital signal 204', for example the first point over a specified voltage, is then used in a reverse look up 212 to find a reference pulse curve 214, which is used to determine the precise start time 216 for the detected pulse.

It is noted that although the disclosed algorithm with a 70 MHz ADC may produce a slightly lower timing resolution than an analog CFD method, the timing resolution will improve as the ADC technologies improve. Given that the resolution of a CFD does not scale with technology (CFD performance has remained fairly constant over the last decade or more), the present algorithm is projected to outperform the CFD method with a 500 MHz ADC (available now in parallel ADCs, and expected soon in serial ADCs).

It will be appreciated that even in situations where the present method does not match CFDs in timing resolution, CFD methods require per-channel custom logic, in fixed ASICs. The presented, all-digital method avoids this cost, which is substantial in PET scanners, which may include, for example 128 channels per FPGA.

In summary, PET is an application well suited to FPGAs. FPGAs are ideal for developing algorithms such as digital timing, but they also provide most of the pieces needed for an advanced data acquisition and processing system for PET. The present system utilizes the reconfigurability of FPGAs to develop a tuning algorithm that, under the control of the microprocessor, can adjust gains and set registers to accommodate for variances in different parts of the scanner, and the sophisticated I/O to interface with fast serial ADCs, allows processing more channels. These channels can also be processed in parallel in the reconfigurable fabric, which increases the count rate that the scanner can handle. The increase in computing power of modern FPGAs over the earlier generation allows us to implement timing in the FPGA and eliminate the ASICs.

A new, all-digital timing pickoff mechanism that demonstrates better timing resolution than current state-of-the-art approaches when coupled with current and future ADC technologies is also disclosed. Many of the features of modern FPGAs can be harnessed to support a complete, complex signal processing system in an important electronics domain.

Although the method described above produces very good timing pick off results, it is contemplated that the timing pick off may be further improved by using an alternative method for determining a suitable reference pulse, while retaining the amplitude normalization and timing lookup technique discussed above. In an alternative method, the FPGAs are configured to capture and store many event pulses and utilize these pulses to form the reference pulse. In particular, the captured data will be scattered by differing amplitudes and sub-sampling rate time shifts (i.e., the pulse start time relative to the pulse sample interval). A two-step process is used to form a composite reference pulse. First, the received pulses are normalized in amplitudes as discussed above, and an initial reference pulse is generated by averaging the data. Then, each individual pulse is aligned to this reference pulse by shifting in time, even iterating until all curves have been best correlated. The aligned pulses can then be used to form a final reference pulse. The final reference pulse may then be used in place of the two-exponential reference pulse curve discussed above.

Although the disclosed method for accurately and digitally estimating the start time for detected analog pulse signals was developed for positron emission tomography, it will be apparent to persons of skill in the art that the general method may be used to very accurately estimate the start time of pulse signals in other contexts, and the method is therefore believed to be suitable for use in other applications wherein high-speed event start information is desired.

While illustrative embodiments have been illustrated and described, it will be appreciated that various changes can be made therein without departing from the spirit and scope of the invention.

The invention claimed is:

1. A method for estimating the start time of an electronic pulse generated in response to a detected event, the method comprising:
   providing a detector that detects an external event and responds to the detected event by generating an electronic analog pulse signal;
      using a plurality of digitized analog pulses to generate a composite reference pulse to represent analog pulse signals generated by the detector;
   receiving an analog pulse signal generated by the detector;
   digitizing the received analog pulse signal to produce a digital pulse signal having an amplitude;
   normalizing the digital pulse signal amplitude based on a computed area of the digital pulse signal;
   comparing at least one point of the normalized digital pulse signal to the composite reference pulse to estimate a start time of the received analog pulse signal; and
   recording a time stamp indicating the estimated start time of the received analog pulse signal.

2. The method of claim 1, wherein using the plurality of digitized analog pulses to generate the composite reference pulse to represent the analog pulse signals generated by the detector comprises:
   averaging the plurality of digitized analog pulses to generate an initial reference pulse; and
   aligning each of the plurality of digitized analog pulses to the initial reference pulse to generate the composite reference pulse.

3. The method of claim 2, wherein aligning each of the plurality of digitized analog pulses to the initial reference pulse comprises:
   using time shifting to align the plurality of digitized analog pulses to the initial reference pulse.

4. The method of claim 3, further comprising:
   repeating the averaging and the aligning one or more times to improve the quality of the composite reference pulse.

5. The method of claim 1, wherein the received analog pulse signal is generated by a silicon photomultiplier.

6. The method of claim 1, further comprising filtering the received analog pulse signal with a low-pass filter.

7. The method of claim 1, wherein the detector comprises a scintillator crystal coupled to one of a photomultiplier tube, an avalanche photodiode and a silicon photomultiplier.

8. A method for estimating the start time for a pulse detected in positron emission tomography comprising:
   providing a detector for detecting photons having an energy of about 511 KeV, and generating an analog pulse signal in response;
   using a plurality of digitized analog pulses to generate a composite reference pulse to represent analog pulse signals generated by the detector;
   receiving an analog pulse signal generated by the detector;
   digitizing the received analog pulse signal to produce a digital pulse signal having an amplitude;
   normalizing the digital pulse signal amplitude based on a computed area of the digital pulse signal;
   comparing at least one point of the normalized digital pulse signal to the composite reference pulse to estimate a start time of the received analog pulse signal; and
   recording a time stamp indicating the estimated start time of the received analog pulse signal.

9. The method of claim 8, wherein using the plurality of digitized analog pulses to generate the composite reference pulse to represent the analog pulse signals generated by the detector comprises:
   averaging the plurality of digitized analog pulses to generate an initial reference pulse; and
   aligning each of the plurality of digitized analog pulses to the initial reference pulse to generate the composite reference pulse.

10. The method of claim 9, wherein aligning each of the plurality of digitized analog pulses to the initial reference pulse comprises:
    using time shifting to align the plurality of digitized analog pulses to the initial reference pulse.

11. The method of claim 10, further comprising:
    repeating the averaging and the aligning one or more times to improve the quality of the composite reference pulse.

12. The method of claim 8, wherein the received analog pulse signal is generated by a silicon photomultiplier.

13. The method of claim 8, further comprising filtering the received analog pulse signal with a low-pass filter.

14. The method of claim 8, wherein the detector comprises a scintillator crystal coupled to one of a photomultiplier tube, an avalanche photodiode and a silicon photomultiplier.

15. The method of claim 8, further comprising providing front-end electronics comprising an analog to digital converter configured to digitize the received analog pulse signal, and a field programmable gate array configured to process the digital pulse signal.

16. The method of claim 15, wherein a resolution of the estimated start time of the received analog pulse signal is less than a sample time used for digitizing the received analog pulse signal.

17. A method for identifying coincidence pairs in positron emission tomography comprising:
- detecting a plurality of photons and generating an analog pulse signal in response to each detected photon, using a plurality of detectors arranged annularly such that some of the detectors are disposed within a field of view of each other;
- using a plurality of digitized analog pulses to generate a composite reference pulse to represent analog pulse signals;
- digitizing the analog pulse signals to produce digital pulse signals having an amplitude;
- normalizing each digital pulse signal's amplitude based on a computed area of the digital pulse signal;
- comparing at least one point of the normalized digital pulse signal to the composite reference pulse to estimate a start time of the analog pulse signal for each analog pulse signal;
- recording a time stamp indicating the estimated start time of the analog pulse signals; and
- comparing time stamps of analog pulse signals from detectors disposed within the field of view of each other to identify coincidence pairs.

18. The method of claim 17, wherein using the plurality of digitized analog pulses to generate the composite reference pulse to represent the analog pulse signals comprises:
- averaging the plurality of digitized analog pulses to generate an initial reference pulse; and
- aligning each of the plurality of digitized analog pulses to the initial reference pulse to generate the composite reference pulse.

19. The method of claim 18, wherein aligning each of the plurality of digitized analog pulses to the initial reference pulse comprises:
- using time shifting to align the plurality of digitized analog pulses to the initial reference pulse.

20. The method of claim 19, further comprising:
- repeating the averaging and the aligning one or more times to improve the quality of the composite reference pulse.

21. The method of claim 17, further comprising filtering the received analog pulse signal with a low-pass filter.

22. The method of claim 17, wherein the detectors comprise a scintillator crystal coupled to one of a photomultiplier tube, an avalanche photodiode and a silicon photomultiplier.

23. The method of claim 17, further comprising providing front-end electronics comprising an analog to digital converter configured to digitize the analog pulse signals, and a field programmable gate array configured to process the digital pulse signals.

24. The method of claim 23, wherein a resolution of the estimated start time of the analog pulse signals is less than a sample time used for digitizing the analog pulse signals.

25. A positron emission tomography scanner comprising:
- a plurality of detectors arranged in an annular array, each detector comprising at least one scintillator and at least one photomultiplier;
- a front-end electronics system that is operable to receive analog signals from the detector photomultipliers, the front-end electronics systems including analog to digital converters that convert the received analog signals into digital signals and field programmable gate arrays that receive the digital signals and calculate start times of the analog signals;
- wherein the field programmable gate arrays calculate the start times of the analog signals by:
  - (i) using a plurality of digitized analog pulses to generate a composite reference pulse to represent the analog signals;
  - (ii) for each of the digital signals, normalizing the digital signal's amplitude based on a computed area of the digital signal;
  - (iii) for each of the normalized digital signals, comparing at least one point of the normalized digital signal to the composite reference pulse to estimate the start time of the analog signal.

26. The positron emission tomography scanner of claim 25, wherein using the plurality of digitized analog pulses to generate the composite reference pulse to represent the analog signals comprises:
- averaging the plurality of digitized analog pulses to generate an initial reference pulse; and
- aligning each of the plurality of digitized analog pulses to the initial reference pulse to generate the composite reference pulse.

27. The positron emission tomography scanner of claim 25, wherein each of the at least one photomultipliers comprises one of a photomultiplier tube, a silicon photomultiplier and an avalanche photo diode.

28. The positron emission tomography scanner of claim 25, further comprising a filter configured to filter the analog signal before it is digitized.

\* \* \* \* \*